(12) United States Patent
Porubcan

(10) Patent No.: US 9,011,843 B2
(45) Date of Patent: *Apr. 21, 2015

(54) FORMULATIONS INCLUDING MONOVALENT ALGINATE TO ENHANCE EFFECTIVENESS OF ADMINISTERED DIGESTIVE ENZYMES

(75) Inventor: Randolph S. Porubcan, Victoria, MN (US)

(73) Assignee: Master Supplements, Inc., Victoria, MN (US)

( * ) Notice: Subject to any disclaimer, the term of this patent is extended or adjusted under 35 U.S.C. 154(b) by 1606 days.

This patent is subject to a terminal disclaimer.

(21) Appl. No.: 11/956,583

(22) Filed: Dec. 14, 2007

(65) Prior Publication Data

US 2008/0145355 A1 Jun. 19, 2008

Related U.S. Application Data

(60) Provisional application No. 60/874,937, filed on Dec. 14, 2006.

(51) Int. Cl.

| A61K 38/48 | (2006.01) |
|---|---|
| A61K 31/733 | (2006.01) |
| A61K 31/734 | (2006.01) |
| A61K 49/04 | (2006.01) |
| A61K 9/48 | (2006.01) |
| A61K 38/47 | (2006.01) |
| A61K 38/46 | (2006.01) |

(52) U.S. Cl.
CPC .............. *A61K 38/48* (2013.01); *A61K 9/4866* (2013.01); *A61K 38/47* (2013.01); *A61K 38/465* (2013.01); *A61K 38/4873* (2013.01); *A61K 31/733* (2013.01); *A61K 31/734* (2013.01)

(58) Field of Classification Search
CPC ..................................................... A61K 31/734
USPC ....................................................... 424/94.21
See application file for complete search history.

(56) References Cited

U.S. PATENT DOCUMENTS

| 4,859,471 | A | * | 8/1989 | Fulberth et al. ............... 424/480 |
| 4,927,638 | A | * | 5/1990 | Bykadi et al. ................. 424/455 |
| 4,950,600 | A | * | 8/1990 | Tanaka et al. ................. 435/178 |
| 5,578,304 | A | * | 11/1996 | Sipos .......................... 424/94.1 |
| 7,122,370 | B2 | | 10/2006 | Porubcan |
| 7,229,818 | B2 | | 6/2007 | Porubcan |
| 2002/0076438 | A1 | * | 6/2002 | Ullah et al. ................... 424/469 |
| 2004/0175389 | A1 | * | 9/2004 | Porubcan ................... 424/184.1 |
| 2004/0191237 | A1 | * | 9/2004 | Davidson et al. ............ 424/94.2 |
| 2005/0106132 | A1 | | 5/2005 | Porubcan |
| 2007/0048295 | A1 | * | 3/2007 | Chen et al. ................. 424/93.45 |
| 2008/0187525 | A1 | | 8/2008 | Porubcan |

OTHER PUBLICATIONS

Narayanan et al., 2002, Biomacromolecules, 13, 2465-2471.*

* cited by examiner

*Primary Examiner* — Sharmila G. Landau
*Assistant Examiner* — Sheridan Macauley
(74) *Attorney, Agent, or Firm* — Eric P. Mirabel

(57) ABSTRACT

Disclosed are alginate formulations that help protect digestive enzymes in the formulations from denaturation during passage through the acidic stomach environment, and from other sources, following ingestion. The formulation changes consistency to permit release of the enzymes in the less-acidic gut. They contain monovalent alginate salts (sodium, potassium and ammonium alginate) but are designed to not include significant quantities of compounds which would generate divalent ions and thereby convert the monovalent alginate to a divalent alginate when exposed to aqueous solution. A buffering agent that does not react with the digestive enzymes or the monovalent alginate, and which does not generate divalent ions on exposure to aqueous solution, can be included. A chelating agent which binds divalent ions may be administered with the formulation. Additionally, the formulation may be admixed with inert excipients suitable for oral delivery. It is preferable that the ingredients are dried before formulation.

35 Claims, No Drawings

FORMULATIONS INCLUDING MONOVALENT ALGINATE TO ENHANCE EFFECTIVENESS OF ADMINISTERED DIGESTIVE ENZYMES

RELATED APPLICATIONS

This application claims priority to U.S. Provisional application No. 60/874,937, filed Dec. 14, 2006.

BACKGROUND

It is known that digestive enzymes administered to mammals can remedy enzyme deficiency caused by aging or various diseased conditions, including those affecting the pancreas, such as cystic fibrosis, pancreatitis and pancreatic enzyme deficiency. Oral administration of supplemental digestive enzymes can be a solution. However, digestive enzymes produced by the pancreas are released into the duodenum, the pH of which is close to neutral or slightly alkaline. Under these pH conditions, these enzymes are active and digestion of the food by the enzymes proceeds normally in the upper segment of the intestine. However, when digestive enzymes are administered exogenously to the patient, the gastric conditions in the stomach, including the highly acidic environment therein, the presence of trypsin and pepsin, and, sometimes, interactions with other foods or stomach contents, will result in inactivating the enzymes (as a result of denaturation—i.e., a change in the enzyme's protein structure).

Such denaturation reactions have negatively inhibited wide-spread use of digestive enzyme supplements. Weakly formulated products are not effective, and not worth buying for the consumer, and more robust products (that allow some activity) sell at premium prices, and are often not affordable. Relatively low-cost formulations which permit digestive enzymes such as proteases, amylases, lipases and fiber digesting enzymes to be effectively delivered into the intestinal tract with reduced denaturation, offer increased effectiveness and enhanced market acceptance, permitting those suffering enzyme deficiencies the opportunity for treatment.

SUMMARY

Disclosed are formulations for protecting digestive enzymes from denaturation in vivo. The formulation includes dry mixtures of digestive enzymes with water soluble monovalent alginates, including sodium, potassium or ammonium alginate, and wherein the formulation does not includes significant quantities of compounds would generate significant quantities of divalent ions and thereby convert the monovalent alginate to a divalent alginate, when exposed to aqueous solution. Divalent ions, and divalent alginates, should be excluded from the mixture, to the extent possible and practical, it being understood that trace amounts would always remain. The mixture is preferably encapsulated in a suitable pharmaceutical grade capsule approved for human or animal consumption, such as a gelatin, cellulose, or a Hydroxypropyl Methylcellulose (HPMC) capsule (or made into a tablet).

When such capsules are subject to the acidic environment of the stomach (or otherwise placed in an environment at the stomach pH of about 1.6-2.0) an essentially impervious gel forms as the stomach acid (primarily hydrochloric acid) dissolves the capsule material and reacts with the exposed monovalent alginate in the formulation. See U.S. Pat. Nos. 7,122,370; 7,229,818 (incorporated by reference). The portion of monovalent alginate that is exposed to and reacts with the acid converts immediately to insoluble alginic acid, forming a somewhat rigid gel, impervious to acid, that encases the remainder of the formulation, including the digestive enzymes, thereby isolating it from stomach acid and hostile agents.

The alginic acid gel remains intact at low pH (such as a pH below about 2.0 to 4.0) but reverts back to soluble monovalent alginate above a pH of about 5.0 to 7.5. Upon arriving in the small intestine, where the pH is in the range of 6.0 to 8.0, the alginic acid gel dissolves, reverting back to a soluble monovalent alginate salt releasing the previously sequestered enzymes unharmed to begin food digestion.

Divalent salts of alginic acid, such as calcium or magnesium alginate, are insoluble and, therefore, cannot effectively form the protective alginic acid gel. Furthermore, the presence of significant quantities of divalent ions (with or without monovalent alginate salt(s), such as sodium alginate) in the formulation, results in the monovalent alginate being converted to a divalent alginate, which is insoluble and unsuitable.

Nevertheless, the portion (generally in the range of 5-10% of the total enzyme weight) in the formulation that is exposed to stomach acid before or during formation of the alginic acid gel may be denatured by the acid. Such denaturation can be inhibited by adding a pH buffering agent to the formulation, preferably one that does not react with the enzymes or alginate components. Buffers producing divalent ions such as salts of calcium or magnesium are not acceptable because they react to form insoluble alginates. Buffers producing significant carbonate or bicarbonate anions are not acceptable because they cause effervescence when exposed to acid, which degrades the integrity of the alginic acid gel. A number of non-reactive buffers, including sodium, potassium or ammonium salts of glycerol phosphate, (including Glycerol phosphate disodium salt from Sigma (catalog No. G 6501)) are suitable and can be combined in the formulation with the digestive enzymes and monovalent alginates to provide additional protection for the formulation against lowered pH. The amount of non-reactive buffer used in the formulations of the present invention typically ranges from 0.1 to 20% by weight of the formulation, but may be higher for applications employing enzymes that are abnormally sensitive to acidic pH.

DETAILED DESCRIPTION

When capsules including the formulations described herein are ingested and enter the stomach, an impervious alginic acid gel forms as the capsule material dissolves and stomach acid reacts with the monovalent alginate salts that are proximal to the inner wall of the capsule material. The capsule material acts as a mold that allows a structured gel to form. This gel of alginic acid is insoluble, semi-rigid and relatively strong and acts to contain the majority of the digestive enzymes in a protected state as long as they remain in an acidic environment.

Depending on the motility within the stomach, composition of food contained in the stomach, water content, and other factors, the alginic acid gel may or may not stay intact as a cylindrical structure but may fragment. Such fragments have inner structure that still confers significant protection until reaching the small intestine, where they dissolve, as the insoluble alginic acid gel converts back to soluble monovalent alginate, and releases the enzymes.

One can also dry the monovalent alginates prior to use so they do not contribute moisture in the formulation. Moisture can be destabilizing to dry enzymes and result in decreased shelf-life. In addition, decreased moisture contributes to more efficient formation of the protective alginic acid gel layer rendering it more rigid. Typically, commercially available alginates have moistures in the range of 8-15%, and are generally more suitable if dried to below 6% moisture. Drying must not denature the alginate polymeric structure, needed for forming the protective alginic acid gel. Low temperature vacuum drying or infrared convection drying are generally suitable methods for drying the monovalent alginates, as are other methods that do not result in their denaturation. A suitable vacuum oven for drying is Lab-Line Model No. 3620 from Lab-Line Instruments, Inc., Melrose Park, Ill. Typical drying parameters are 60-70° C. for 12-18 hours at a vacuum of 27-28 inches of mercury, or until the final moisture content is equal to or less than 6%.

The amount of monovalent alginate required to adequately protect dry enzymes in formulations of the present invention ranges from 10-90% of the weight of the formulation, with a preferred range from 20-40% of the formulation. Suitable commercial monovalent alginates for use in the present invention are Algin-900 (TIC Gums) and Keltone HV (ISP). Commercial alginates are prepared from different seaweed sources and vary in their ratio of mannuronic acid to guluronic acid (M:G ratio). Alginates prepared from giant kelp, *Macrocystis pyrifera*, have high M values while alginates produced from *Laminaria hyperborean* have high G values. G type alginates are preferred since they produce a stronger alginic acid gel than the M alginates; but both alginate types are suitable for the formulations described herein.

The amount of dry digestive enzymes used depends on the strength or activity of each enzyme that is required in the formulation, but will typically range from 10-90% of the formulation. Single digestive enzymes or blends of different enzymes can be used in the formulations. Enzymes known to be particularly sensitive to stomach acid, e.g., enzymes nattokinase and serrapeptase, can be effectively protected by the formulations herein. The following list of commercial enzymes represent examples of some of the digestive enzymes suitable for the formulation:

| ENZYME | ORIGIN | TYPICAL ACTIVITY |
|---|---|---|
| Alpha Galactosidase | *Aspergillus niger* | 15,000 GalU/g |
| Amyloglucosidase | *Aspergillus niger* | 1,000 AG/g |
| Bacterial Alpha Amylase | *Bacillus subtilis* | 300,000 BAU/g |
| Beta Glucanase | *Trichoderma longibrachiatum* | 3,000 BGU/g |
| Cellulase | *Trichoderma longibrachiatum* | 150,000 CU/g |
| Cellulase AN | *Aspergillus niger* | 50,000 CU/g |
| Fungal Alpha Amylase | *Aspergillus oryzae* | 100,000 SKB/g |
| Fungal Lactase | *Aspergillus oryzae* | 100,000 ALU/g |
| Yeast Lactase | *Kluyveromyces lactis* | |
| Hemicellulase | *Aspergillus niger* | 400,000 HCU/g |
| Invertase | *Saccharomyces cerevisiae* | 200,000 Summer U/g |
| Pectinase | *Aspergillus niger* | 500,000 AJDU/g |
| Xylanase | *Trichoderma longibrachiatum* | 150,000 XU/g |
| Bromelain Protease | *Ananas comosus* | 2,000 GDU/g |
| Fungal Protease | *Aspergillus oryzae* | 400,000 HU/g |
| Neutral Protease | *Bacillus subtilis* | 2,000,000 PC/g |
| Papain Protease | *Carica papaya* | 800 TU/mg |
| Peptidase | *Aspergillus oryzae* | 500 LAP/g |
| Lipase | *Rhizopus oryzae* | 150,000 FIP/g |
| Lipase | *Candida rugosa* | 200,000 FIP/g |
| Lipase AN | *Aspergillus niger* | 20,000 FIP/g |
| Phytase | *Aspergillus niger* | 1,500 U/g |
| Pancreatin | Hog or bovine pancreas | mixed enzymes |

The above enzymes can be obtained from Bio-Cat, Inc., Troy, Va., USA.

If the formulations require inert excipient ingredients to complete the formulation, there are a variety of inert, dry, pharmaceutical or food grade products that can be used. Examples are microcrystalline cellulose, silica, resistant starches and prebiotic carbohydrates such as inulin. While many types of inert excipients can be used, preferred excipients would be those with very low moisture contents. Avicel PH112 brand microcrystalline cellulose from FMC is an example of an excipient with a total moisture content below about 2%. Syloid 63 FP from WR Grace is an example of a silica based excipient, with a moisture content less than 1%, which can be used with Avicell PH112 in the formulations. When it is not required to use any microcrystalline cellulose or other bulk excipient in a formulation, such as might be the case when high activity levels of enzymes are desired, it is still recommended that a silica ingredient such as Syloid 63 FP be added at 1-2% of the formulation to improve the flow characteristics of the powder, to thereby enhance capsule filling. Furthermore, it may also be required under commercial capsule filling conditions to utilize magnesium stearate at 1-2% in the formulations to enhance lubrication of the powder blend, for more efficient capsule filling.

Packaging of capsules filled with formulations of the present invention should be carried out in amber glass bottles or hermetically sealed foil packages of high quality to insure maximum shelf-life of the finished product. Addition of moisture and oxygen absorption packets inside the bottles or foil packets helps to maximize shelf-life.

Chelating agents such as EDTA, sodium hexametaphosphate, tetrasodium pyrophosphate or sodium citrate can be co-administered with the formulations to inhibit premature conversion of soluble alginates in the duodenum to insoluble divalent alginates, that may delay or complicate the release of the enzymes. Preferably these chelating agents, which effectively bind divalent ions such as calcium and magnesium, should be consumed separately in capsule or tablet form, prior to consuming capsules containing the enzyme formulations. Any of the above mentioned chelating agents when consumed at levels of 250-1500 mg per dose would sufficiently reduce the formation of divalent alginates.

The formulations can be prepared according to the following manufacturing steps, with more details and conditions set forth in the examples:

1. Prepare dry commercial monovalent alginate salts, preferably sodium alginate, by low temperature vacuum oven drying or infrared convection drying that reduces the moisture content below 6%, utilizing conditions that do not denature the polymeric structure of the alginate.
2. Mix the dry alginate with high quality dry digestive enzymes in a double cone or paddle/ribbon type mixer under conditions of low humidity, e.g., humidity below 25%. The preferred amount of alginate to use is in the range of 15-40% of the weight of the total blend, excipients and/or buffers can be added prior to mixing the alginate-enzyme mixture so that only one mixing step is required. Mixing times should be in the range of 5-20 minutes to avoid over-mixing which can otherwise result in un-mixing of the blend.
3. The blended product should be promptly filled into capsules after blending, such as HPMC, cellulose or gelatin capsules. This should also be done under conditions of low humidity. Running the blended powder through a 12-14 mesh screen after blending but prior to capsule filling may facilitate the capsule filling process.
4. Filled capsules should be packaged in air tight containers such as amber glass bottles or foil packages containing moisture and oxygen absorption packets.

EXAMPLE I

A digestive enzyme formulation as described herein was prepared as follows:
1. Keltone HV brand sodium alginate from ISP, Inc. was dried in a Lab-Line vacuum oven to a moisture content of 5.5%, the oven temperature was not allowed to exceed 70° C. Drying time was 18 hours at 28" of vacuum.
2. A blend of commercial digestive enzymes (EC-1A obtained from Bio-Cat, Inc. of Troy, Va.) contained the following enzymes: Bromelain 800 GDU/g, Papain 237 TU/mg, Lipase 33,600 FIP/g, Fungal Protease 32,000 HU/g.
3. Avicel PH112 brand microcrystalline cellulose was obtained from FMC, Syloid 63 FP brand silica from W. R. Grace and Glycerol phosphate disodium salt from Sigma-Aldrich.
4. The following formulation was prepared from the above ingredients in a lab scale stainless steel paddle mixer: 500 g EC-1A Enzyme Blend+260 g Avicel PH112+200 g dry Keltone HV+20 g Syloid 63+20 g Disodium glycerol phosphate. The mixture was blended for 10 minutes at 60 rpm and then hand filled into size "0" HPMC Vcaps from Capsugel, to a net weight of 400 mg/capsule.
5. The capsules were then tested for enzyme activity with no immersion (control 1) and after immersion (test 1) in simulated gastric juice (composition: 1 liter distilled water+2 g NaCl+7.0 ml 37% HCl, pH=1.6). Immersion in simulated gastric juice was carried out with the capsules submersed in a beaker of the juice, 10 capsules total, held under by a stainless steel screen, while stirring the juice magnetically at 90 rpm for 60 minutes at 37° C. The pH in the beaker was 1.7 during the test. After the 60 minute period, the remaining capsules (or fragments) were dissolved by raising the pH of the beaker contents to 7.5 with a 10% NaOH solution followed by assaying for enzyme activity (four separate assays). For capsules that were not immersed in gastric juice, they (contents of 10 capsules) were dissolved directly in 0.2% saline at pH 7.5 and assayed by the same four enzyme assays.

Results 1A: Enzyme activities on capsules with no immersion at pH 1.7 (control 1):
Total Protease by HUT (Hemoglobin Units/Tyrosine Basis) test=166,059 HUT/g.
Total Protease by PU (Papain Units) test=11,065,000 PU/g.
Total Protease by PC (Bacterial Protease Units)=226,730 PC/g
Lipase by FIP (FCC Lipase units)=12,676 FIP/g
Results 1B: Enzyme activities on capsules after immersion at pH 1.7 (test 1):*
Total Protease by HUT test=151,114 HUT/g (9% loss)
Total Protease by PU (Papain Units) test=10,179,800 PU/g (8% loss).
Total Protease by PC (Bacterial Protease Units)=204,057 PC/g (10% loss).
Lipase by FIP (FCC Lipase units)=11,662 FIP/g (8% loss).
Conclusion: The % loss in enzyme activity, average of 4 tests, test vs control, was 8.75%.

*Note: The enzyme tests used in Example I were not the tests used by the supplier (Bio-Cat, Inc.) of the EC-1A enzyme blend with the exception of the FIP test for lipase which was the same; the supplier did not measure the enzyme activities once the blend had been produced but rather, measured the individual enzyme activity prior to making the blend. The tests used in our Example I were selected because they were better able to show proteolytic activity by three different assay techniques on enzymes in the blend.

EXAMPLE II

The same procedure was followed as for Example I except the sodium alginate in step 4 (Keltone HV) was replaced by additional Avicel PH112, thus producing a formulation without acid protecting monovalent alginate. The formulation had the following composition:
500 g EC-1A Enzyme Blend+460 g Avicel PH112+20 g Syloid 63+20 g Disodium glycerol phosphate. The mixture was blended for 10 minutes at 60 rpm and then hand filled into size "0" HPMC Vcaps from Capsugel to a net weight of 400 mg/capsule.

The capsules were tested for enzyme activity after immersion (test 2) in simulated gastric juice (composition: 1 liter distilled water+2 g NaCl+7.0 ml 37% HCl, pH=1.6). Immersion in simulated gastric juice was carried out with the capsules submersed in a beaker of the juice, 10 capsules total, held under by a stainless steel screen, while stirring the juice magnetically at 90 rpm for 60 minutes at 37 C. The pH in the beaker was 1.65 during the test. After the 60 minute period, the remaining capsules (or fragments) were dissolved by raising the pH of the beaker contents to 7.5 with a 10% NaOH solution followed by assaying for enzyme activity (four separate assays).
Results 2A: Enzyme activities on capsules after immersion at pH 1.65 (test 2):
Total Protease by HUT test=66,424 HUT/g (60% loss vs control 1—see Example 1).
Total Protease by PU (Papain Units) test=4,979,250 PU/g (55% loss vs control 1).
Total Protease by PC (Bacterial Protease Units)=72,554 PC/g (68% loss vs control 1).
Lipase by FIP (FCC Lipase units)=2,282 FIP/g (82% loss vs control 1).
Conclusion: The % loss in enzyme activity, average of 4 tests, test 2 vs control 1, was 66.25%. This indicates that the protection conferred by the sodium alginate in Example I is significant.

EXAMPLE III

A digestive enzyme formulation employing the discoveries of the present invention was prepared by the following technique:
1. Keltone HV brand sodium alginate from ISP, Inc. was dried in a Lab-Line vacuum oven to a moisture content of 5.0%, the oven temperature was not allowed to exceed 70 C. Drying time was 19 hours at 28" of vacuum.
2. A blend of commercial digestive enzymes referred to as EC-2B was obtained from Bio-Cat, Inc. of Troy, Va. containing the following enzymes: Fungal Alpha Amylase 40,000 SKB/g, Cellulase 24,000 CU/g, Hemicellulase 51,200 HCU/g, Pectinase 60,000 AJDU/g, Alpha Galactosidase 1,320 GalU/g, Glucoamylase 48 AG/g, Fungal Lactase 4,000 ALU/g, and Invertase 3,200 Summer U/g.

3. Avicel PH112 brand microcrystalline cellulose was obtained from FMC, Syloid 63 FP brand silica from W. R. Grace and Glycerol phosphate disodium salt from Sigma-Aldrich.
4. The following formulation was prepared from the above ingredients in a lab scale stainless steel paddle mixer: 500 g EC-2B Enzyme Blend+160 g Avicel PH112+300 g dry Keltone HV+20 g Syloid 63+20 g Disodium glycerol phosphate. The mixture was blended for 10 minutes at 60 rpm and then hand filled into size "0" HPMC Vcaps from Capsugel to a net weight of 410 mg/capsule.
5. The capsules were then tested for enzyme activity with no immersion (control 2) and after immersion (test 3) in simulated gastric juice (composition: 1 liter distilled water+2 g NaCl+7.0 ml 37% HCl, pH=1.6). Immersion in simulated gastric juice was carried out with the capsules submersed in a beaker of the juice, 10 capsules total, held under by a stainless steel screen, while stirring the juice magnetically at 90 rpm for 60 minutes at 37 C. The pH in the beaker was 1.75 during the test. After the 60 minute period, the remaining capsules (or fragments) were dissolved by raising the pH of the beaker contents to 7.5 with a 10% NaOH solution followed by assaying for enzyme activity (four separate assays). For capsules that were not immersed in gastric juice they (contents of 10 capsules) were dissolved directly in 0.2% saline at pH 7.5 and assayed by the same four enzyme assays. Only four of the eight enzymes in the blend EC-2B were assayed due to problems encountered with assaying multiple enzymes in a blend.

Results 3A: Enzyme activities on capsules with no immersion at pH 1.7 (control 2):
Total Alpha Galactosidase in GalU/g by FCC method=610 GalU/g.
Total Cellulase in CU/g by FCC method=11,200 CU/g
Total Hemicellulase in HCU/g by FCC method=23,600 HCU/g.
Total Lactase in ALU/g by FCC method=1,700 ALU/g.
Results 3B: Enzyme activities on capsules after immersion at pH 1.7 (test 3):
Total Alpha Galactosidase in GalU/g, FCC method=590 GalU/g (3.3% loss vs cont. 2)
Total Cellulase in CU/g, FCC method=11,000 CU/g (1.8% loss vs control 2).
Total Hemicellulase in HCU/g, FCC method=23,100 HCU/g (2.1% loss vs control 2).
Total Lactase in ALU/g by FCC method=1,400 ALU/g (17.6% loss vs control 2).
Conclusion: With the exception of lactase which lost 17.6%, the losses of the other three enzymes were negligible. The 30% sodium alginate used in the formulation for this Example III provided significant acid protection.

EXAMPLE IV

The same procedure was followed as for Example III except the sodium alginate in step 4 (Keltone HV) was replaced by additional Avicel PH112, thus producing a formula without the acid-protecting alginate. The formulation had the following composition:
500 g EC-2B Enzyme Blend+460 g Avicel PH112+20 g Syloid 63+20 g Disodium glycerol phosphate. The mixture was blended for 10 minutes at 60 rpm and then hand filled into size "0" HPMC Vcaps from Capsugel to a net weight of 390 mg/capsule.
The capsules were tested for enzyme activity after immersion (test 4) in simulated gastric juice (composition: 1 liter distilled water+2 g NaCl+7.0 ml 37% HCl, pH=1.6). The capsules were submersed in a beaker of the juice, 10 capsules total, held under by a stainless steel screen, while stirring the juice magnetically at 90 rpm for 60 minutes at 37° C., the pH was 1.7. After the 60 minute period, the remaining capsules (or fragments) were dissolved by raising the pH of the beaker contents to 7.5 with a 10% NaOH solution. Thereafter, four separate assays were conducted for enzyme activity.
Enzyme activities on capsules after immersion at pH 1.7 (test 4): Total Alpha Galactosidase in GalU/g, FCC method=190 GalU/g (69% loss vs control 2);
Total Cellulase in CU/g, FCC method=8,200 CU/g (25.4% loss vs control 2).
Total Hemicellulase in HCU/g, FCC method=17,100 HCU/g (25.9% loss vs control 2).
Total Lactase in ALU/g, FCC method=250 ALU/g (82% loss vs. control 2).
Results: The percentage loss in enzyme activity, average of 4 tests, test 4 vs control 2, was 50.6%—a significant loss compared to the relatively small losses reported in Example 3, indicating that four (of 8 total) enzymes present in the EC-2B blend are negatively affected by immersion in pH 1.7 simulated gastric juice, for one hour when not protected by sodium alginate.

It should be understood that the examples, terms and expressions herein are exemplary only and not limiting, and that the scope of the invention is defined only in the claims which follow, and includes all equivalents of the claimed subject matter.

What is claimed is:

1. A capsule for administration to aid in digestion, consisting essentially of:
   a capsule shell which houses digestive enzymes, and sufficient quantities of monovalent alginate to form a protective coating for the digestive enzymes on exposure to stomach acid, and
   a buffering agent in an amount from 0.1 to 20% by weight of the formulation that does not produce carbonate or bicarbonate ions on exposure to aqueous solution;
   wherein the capsule does not contain or house compounds which, on exposure to aqueous solution, would generate sufficient quantities of divalent ions to convert enough of the monovalent alginate to an insoluble divalent alginate such that the digestive enzymes would not be released from the capsule when the capsule is exposed to conditions in the intestine.

2. The formulation of claim 1 wherein the monovalent alginate is sodium alginate.

3. The formulation of claim 1 wherein the divalent ions include calcium and magnesium ions.

4. The formulation of claim 1 wherein the capsule shell is composed of HPMC, cellulose or gelatin.

5. The formulation of claim 1 wherein the digestive enzymes are selected from the group consisting of:
   Alpha Galactosidase; Amyloglucosidase; Bacterial Alpha Amylase; Beta Glucanase; Cellulase; Cellulase AN; Amylase; Fungal Lactase; Yeast Lactase; Hemicellulase; Invertase; Pectinase; Xylanase; Bromelain Protease; Fungal Protease; Neutral Protease; Papain Protease; Peptidase Aspergillus oryza; Lipase; Lipase AN; Phytase; Pancreatin; nattokinase; and serrapeptase.

6. The formulation of claim 1 wherein in the monovalent alginate the ratio of mannuronic acid to guluronic acid (M:G ratio) is less than 1.

7. The formulation of claim 1 further including one or more of: microcrystalline cellulose, silica, resistant starches and prebiotic carbohydrate.

8. The formulation of claim 7 wherein the prebiotic carbohydrate is inulin.

9. The formulation of claim 7 wherein the silica is synthetic amorphous silica.

10. The formulation of claim 9 wherein the synthetic amorphous silica is 1-2% of the formulation.

11. The formulation of claim 7 further including magnesium stearate.

12. The formulation of claim 11 wherein the magnesium stearate is 1-2% of the formulation.

13. A kit consisting essentially of:
a capsule which houses a formulation consisting of: digestive enzymes, quantities of monovalent alginate making up 20-40% of the weight of the formulation,
and a buffering agent in an amount from 0.1 to 20% by weight of the formulation that does not produce carbonate or bicarbonate ions on exposure to aqueous solution, and wherein the formulation excludes quantities of compounds which, on exposure to aqueous solution, would generate quantities of divalent ions sufficient to convert enough of the monovalent alginate to an insoluble divalent alginate such that the digestive enzymes would not be released from the capsule when the capsule is exposed to conditions in the intestine; and
a chelating agent which binds divalent ions, said chelating agent in a secondary tablet or secondary capsule.

14. The kit of claim 13 wherein the secondary capsule or tablet includes 250-1500 mg of chelating agent.

15. The kit of claim 14 wherein the chelating agent is EDTA, sodium hexametaphosphate, tetrasodium pyrophosphate or sodium citrate.

16. The kit of claim 13 wherein the monovalent alginate is sodium alginate, potassium alginate or ammonium alginate.

17. The kit of claim 13 wherein the divalent ions include calcium and magnesium ions.

18. The kit of claim 13 wherein the capsule is composed of HPMC, cellulose or gelatin.

19. The kit of claim 13 wherein the digestive enzymes are selected from the group consisting of:
Alpha Galactosidase; Amyloglucosidase; Bacterial Alpha Amylase; Beta Glucanase; Cellulase; Cellulase AN; Amylase; Fungal Lactase; Yeast Lactase; Hemicellulase; Invertase; Pectinase; Xylanase; Bromelain Protease; Fungal Protease; Neutral Protease; Papain Protease; Peptidase Aspergillus oryza; Lipase; Lipase AN; Phytase; Pancreatin; nattokinase; and serrapeptase.

20. The kit of claim 13 wherein in the monovalent alginate the ratio of mannuronic acid to guluronic acid (M:G ratio) is less than 1.

21. The kit of claim 13 further including one or more of:
microcrystalline cellulose, silica, resistant starches and prebiotic carbohydrate.

22. The kit of claim 21 wherein the prebiotic carbohydrate is inulin.

23. The kit of claim 21 wherein the silica is synthetic amorphous silica.

24. The kit of claim 23 wherein the synthetic amorphous silica is 1-2% of the formulation.

25. The kit of claim 13 further including magnesium stearate.

26. The kit of claim 25 wherein the magnesium stearate is 1-2% of the formulation.

27. The kit of claim 13 wherein the buffering agents do not include salts of calcium or magnesium.

28. The kit of claim 13 wherein the buffering agents include sodium, potassium or ammonium salts of glycerol phosphate.

29. The kit of claim 28 wherein the sodium, potassium or ammonium salts of glycerol phosphate are mixed with the digestive enzymes and the monovalent alginate.

30. The kit of claim 13, wherein the monovalent alginates have total moisture contents in the range of 8-15%.

31. The kit of claim 30 wherein the monovalent alginates are dried, before adding them to the formulation, to below 6% total moisture content.

32. The kit of claim 31 wherein the monovalent alginates are dried without denaturing the alginate polymeric structure.

33. The kit of claim 32 wherein the monovalent alginates are dried using vacuum drying, at a temperature below that causing denaturation, or infrared convection drying.

34. The kit of claim 13 packaged in amber glass bottles or hermetically sealed foil packages.

35. The kit of claim 13 wherein the packaging further includes moisture and oxygen absorption packets.

* * * * *